US009295669B2

(12) United States Patent
Dhingra et al.

(10) Patent No.: US 9,295,669 B2
(45) Date of Patent: Mar. 29, 2016

(54) COMBINATION THERAPY FOR PROLIFERATIVE DISORDERS

(75) Inventors: Kapil Dhingra, Sparta, NJ (US); Brian Higgins, Fresh Meadows, NY (US); Kenneth Kolinsky, Bloomingdale, NJ (US); Richard J. Lee, New York, NY (US); Brian Lestini, Union City, NJ (US); Kathryn Packman, Bloomfield, NJ (US); Fei Su, Paramus, NJ (US)

(73) Assignee: Hoffman La-Roche Inc., Nutley, NJ (US)

( * ) Notice: Subject to any disclaimer, the term of this patent is extended or adjusted under 35 U.S.C. 154(b) by 117 days.

(21) Appl. No.: 13/313,042

(22) Filed: Dec. 7, 2011

(65) Prior Publication Data
US 2012/0148533 A1 Jun. 14, 2012

Related U.S. Application Data

(60) Provisional application No. 61/422,690, filed on Dec. 14, 2010.

(51) Int. Cl.
| | |
|---|---|
| *A61K 31/535* | (2006.01) |
| *A61K 31/505* | (2006.01) |
| *A61K 38/21* | (2006.01) |
| *A01N 43/54* | (2006.01) |
| *A01N 43/42* | (2006.01) |
| *C07D 413/00* | (2006.01) |
| *C07D 239/02* | (2006.01) |
| *C07D 401/00* | (2006.01) |
| *C07D 403/00* | (2006.01) |
| *C07D 471/02* | (2006.01) |
| *A61K 31/437* | (2006.01) |

(52) U.S. Cl.
CPC .............. *A61K 31/437* (2013.01); *A61K 38/21* (2013.01); *A61K 38/212* (2013.01)

(58) Field of Classification Search
CPC ... A61K 38/21; A61K 38/212; A61K 31/437; A61K 2300/00
See application file for complete search history.

(56) References Cited

U.S. PATENT DOCUMENTS

| | | | |
|---|---|---|---|
| 5,516,807 A | 5/1996 | Hupe et al. | |
| 7,504,509 B2 | 3/2009 | Ibrahim et al. | |
| 7,851,626 B2 | 12/2010 | Ding et al. | |
| 7,863,288 B2 * | 1/2011 | Ibrahim et al. | 514/300 |
| 8,143,271 B2 | 3/2012 | Ibrahim et al. | |
| 8,470,818 B2 | 6/2013 | Ibrahim et al. | |
| 2001/0041712 A1 | 11/2001 | Bissery | |
| 2002/0035091 A1 | 3/2002 | Govindarajan et al. | |
| 2002/0119955 A1 | 8/2002 | Doyle et al. | |
| 2003/0147945 A1 | 8/2003 | Tardi et al. | |
| 2003/0229112 A1 | 12/2003 | Houghton | |
| 2004/0254210 A1 | 12/2004 | Haeberlin et al. | |
| 2005/0176740 A1 | 8/2005 | Spector et al. | |
| 2005/0244407 A1 | 11/2005 | Rose | |
| 2005/0272737 A1 | 12/2005 | Chen et al. | |
| 2005/0276851 A1 * | 12/2005 | Cunningham et al. | 424/468 |
| 2006/0257400 A1 | 11/2006 | Fargnoli | |
| 2007/0026014 A1 | 2/2007 | De Luca | |
| 2007/0110715 A1 | 5/2007 | Grimaldi | |
| 2007/0281041 A1 | 12/2007 | Ramesh et al. | |
| 2008/0193445 A1 | 8/2008 | Goetsch et al. | |
| 2008/0248038 A1 | 10/2008 | Corvinus et al. | |
| 2009/0053206 A1 | 2/2009 | Kandimalla et al. | |
| 2009/0214562 A1 | 8/2009 | Karel | |
| 2009/0269344 A1 | 10/2009 | Siena et al. | |
| 2010/0104567 A1 | 4/2010 | Shiotsu et al. | |
| 2010/0152190 A1 | 6/2010 | Bartkovitz et al. | |
| 2010/0297080 A1 | 11/2010 | Bertelsen et al. | |
| 2010/0310659 A1 | 12/2010 | Desai et al. | |
| 2012/0045433 A1 | 2/2012 | Dhingra et al. | |
| 2012/0045434 A1 | 2/2012 | Dhingra et al. | |
| 2013/0245039 A1 | 9/2013 | Higgins et al. | |

FOREIGN PATENT DOCUMENTS

| | | |
|---|---|---|
| EP | 2 621 516 A2 | 8/2013 |
| KR | 2007/0018109 A | 2/2007 |
| RU | 2179859 C1 | 2/2002 |
| WO | 200603804 A | 2/2006 |
| WO | 2007/002325 | 1/2007 |
| WO | WO-2008/082730 A2 | 7/2008 |
| WO | WO-2008/082730 A3 | 7/2008 |
| WO | 2010/114928 | 10/2010 |
| WO | 2010/120759 | 10/2010 |

(Continued)

OTHER PUBLICATIONS

Goldstein D, et al. The role of interferon in cancer therapy: A current perspective. CA Cancer J. Clin., 1988, vol. 38, p. 258-277.*
Dummer R, et al. Randomized dose-escalation study evaluating peginterferon alfa-2a in patients with metastatic malignant melanoma. J. Clin. Oncol., 2006, vol. 24, No. 7, p. 1188-1194.*
Friesen D.T., et al. Hydroxypropyl methylcellulose acetate succinate-based spray-dried dispersions: An overview. Molecular Pharmaceutics, 2008, vol. 5, No. 6, p. 1003-1019.*

(Continued)

*Primary Examiner* — Robert Landsman
*Assistant Examiner* — Bruce D Hissong
(74) *Attorney, Agent, or Firm* — Morrison & Foerster LLP

(57) ABSTRACT

The present invention relates to a combination therapy of propane-1-sulfonic acid{3-[5-(4-chloro-phenyl)-1H-pyrrolo[2,3-b]pyridine-3-carbonyl-2,4-difluoro-phenyl]-amide}, or a pharmaceutically acceptable salt thereof, and an interferon for treating a patient suffering from a proliferative disorder, in particular a solid tumor, for example, colorectal cancer, melanoma, and thyroid cancer. In particular, the present invention relates to such a therapy wherein the interferon is peginterferon alfa-2a and the disorder is melanoma containing the V600E b-Raf mutation.

11 Claims, 6 Drawing Sheets

(56) References Cited

FOREIGN PATENT DOCUMENTS

| WO | WO-2011/028540 A1 | 3/2011 |
|---|---|---|
| WO | 2012/022677 | 2/2012 |
| WO | 2012/022724 | 2/2012 |

OTHER PUBLICATIONS

Huh, C. et al. A review of US anthropometric reference data (1971-2000) with comparisons to both stylized and tomographic anatomic models. Phys. Med. Biol., 2003, vol. 48, p. 3411-3429).*

"International Search Report PCT/EP2011/072408 mailed Apr. 2, 2012".

Mason, E. (Oct. 23, 2008). "Study Finds BRAF Mutations in Colorectal Cancer Cause Resistance to Anti-EGFR Therapy," *ECCO—The European Cancer Organisation*, 2 Total Pages.

Search Report mailed on Sep. 11, 2013, for Taiwanese Patent Application No. 100129118 filed on Aug. 15, 2011, 2 pages.

Abal et al. (2004). "Enhanced Sensitivity to Irinotecan by Cdk1 Inhibition in the p53-Deficient HT29 Human Colon Cancer Cell Line," *Oncogene* 23:1737-1744.

Chan et al. (Jun. 1996). "Regulation of antigen receptor signal transduction by protein tyrosine kinases," *Curr. Opin. Immunol.* 8(3):394-401.

Cunningham et al. (Jul. 2004). "Cetuximab Monotherapy and Cetuximab Plus Irionotecan in Irinotecan in Irinotecan-Refractory Metastatic Colorectal Cancer," *N. Eng. J. Med.* 351:337-345.

Galal et al. (Mary 15, 2009). "Inherent Resistance to Epidermal growth Factor Receptor Antibodies in Refractory Metastatic Colorectal Cancer," *J. Med. Sci.* 9(4):165-174.

International Search Report mailed on Oct. 20, 2011, for PCT Patent Application No. PCT/EP2011/064050 filed on Aug. 16, 2011, five pages.

International Search Report mailed on Oct. 17, 2011, for PCT Patent Application No. PCT/EP2011/063892 filed on Aug. 12, 2011, four pages.

Kim et al. (2006)."Cetuximab and Irinotecan Interact synergistically to Inhibit the Growth of Orthotopic Anaplastic Thyroid Carcinoma Xenografts in Nude Mice," *Clin. Cancer Res.* :12(2):600-607.

Lee et al. (2012). "MEK'ing the Most of p53 Reactivation Therapy in Melanoma," *J. Investigative Dermatology* 132:263-265.

Mross et al. (2007). "Results from an in Vitro and a Clinical/Pharmacological Phase I Study With the Combination Irinotecan and Sorafenib," *European Journal of Cancer* 43:55-63.

Ouchi et al. (May 2006, e-pub. Dec. 16, 2005). "Antitumor activity of erlotinib in combination with capecitabine in human tumor xenograft models," *Cancer Chemother. Pharmacol.* 57(5):693-702.

Paraiso et al. (May 1, 2012, e-pub. Feb. 20, 2012). "The HSP90 Inhibitor XL888 Overcomes BRAF Inhibitor Resistance Mediated through Diverse Mechanisms," *Clin. Cancer. Res.* 18(9):2502-2514.

Prewett et al. (May 2002). "Enhanced Antitumor Activity of Anti-Epidermal Growth Factor Receptor Monoclonal Antibody IMC-C225 in Combination With Irinotecan (CPT-11) Against Human Colorectal Tumor Xenografts," *Clin. Can. Res.* 8:994-1003.

Rubinstein et al. (2010). "Incidence of the V600K Mutation Among Melanoma Patients with BRAF Mutations, and Potential Therapeutic Response to the Specific BRAF Inhibitor PLX4032," *J. Translational Medicine* 8(67):1-3.

Salerno (Jan. 2010). "Cytostatic Activity of Adenosine Triphosphare-Competitive Kinase Inhibitors in BRAF Mutant Thyroid Carcinoma Cells," *J. Clin. Endocrinology and Metabolism* 95(1):450-455.

Shi et al. (2011). "Combinatorial Treatments That Overcome PDGFRβ-Driven Resistance of Melanoma Cells to $^{V600E}$B-RAF Inhibition," *Cancer Res.* 71:5067-5074.

Tabernero et al. (2008). "Administration of Cetuxiamab Every 2 Weeks in the Treatment of Metastatic Colorectal Cancer: An Effective, More Convenient Alternative to Weekly Administration?"*The Oncologist* 13(2):113-119.

Wright et al. (Jan. 1992). "Relationship between c-erbB-2 protein product expression and response to endocrine therapy in advanced breast cancer." *Br. J. Cancer* 65(1):118-121.

Written Opinion of the International Searching Authority mailed on Oct. 20, 2011, for PCT Patent Application No. PCT/EP2011/064050 filed on Aug. 16, 2011, eight pages.

Written Opinion of the International Searching Authority mailed on Oct. 17, 2011, for PCT Patent Application No. PCT/EP2011/063892 filed on Aug. 12, 2011, seven pages.

Written Opinion of the International Searching Authority mailed on Apr. 2, 2012, for PCT Patent Application No. PCT/EP2011/072408 filed on Dec. 12, 2011, five pages.

Search Report mailed on Jul. 20, 2013, for Taiwanese Patent Application No. 100129120 filed on Aug. 15, 2011, one page.

Yang et al. (Jul. 1, 2010). "RG7204 (PLX4032), a selective BRAFV$^{600E}$ inhibitor, displays potent antitumor activity in preclinical melanoma models," *Cancer Res.* 70(13):5518-5527, correction one page, page No. 9527.

Ryan, C.W. et al. (Aug. 1, 2007). "Sorafenib With Interferon Alfa-2b as First-Line Treatment of Advanced Renal Carcinoma: A phase II Study of the Southwest Oncology Group," *J. Clin. Oncol.* 25(22):3296-3301.

* cited by examiner

COMBINATION THERAPY FOR PROLIFERATIVE DISORDERS

PRIORITY TO RELATED APPLICATIONS

This application claims the benefit of U.S. Provisional Application No. 61/422,690, filed Dec. 14, 2010, which is hereby incorporated by reference in its entirety.

FIELD OF THE INVENTION

The present invention relates to a combination therapy for treating a patient suffering from a proliferative disorder, in particular a solid tumor, for example, colorectal cancer, melanoma, and thyroid cancer, comprising administering to the patient propane-1-sulfonic acid{3-[5-(4-chloro-phenyl)-1H-pyrrolo[2,3-b]pyridine-3-carbonyl]-2,4-difluoro-phenyl}-amide and an interferon.

BACKGROUND OF THE INVENTION

Normally functioning b-Raf is a kinase which is involved in the relay of signals from the cell membrane to the nucleus and is active only when it is needed to relay such signals. Mutant b-Raf containing a V600E mutation, however, is constantly active and thus plays a role in tumor development. Such mutant b-Raf has been implicated in various tumors, for example, colorectal cancer, melanoma, and thyroid cancer.

Propane-1-sulfonic acid{3-[5-(4-chloro-phenyl)-1H-pyrrolo[2,3-b]pyridine-3-carbonyl]-2,4-difluoro-phenyl}-amide (hereafter also referred to as "Compound I") is a b-raf kinase inhibitor that specifically targets mutant b-Raf containing the V600E mutation. This compound is described in WO 2007/002325. Accordingly, such an inhibitor is used in the inhibition of tumors, particularly solid tumors, for example, colorectal cancer, melanoma, and thyroid cancer, which comprise b-Raf having the V600E mutation.

Interferons (IFNs) are naturally occurring proteins that have antiviral, antiproliferative, and immunoregulatory activity. The IFNα family represents the predominant class of IFNs produced by stimulated peripheral blood leukocytes and lymphoblastoid and myeloblastoid cell lines. Interferons downregulate the expression of bFGF. These drugs can be self administered by patients via subcutaneous injection with resultant good pharmacokinetics. For the purpose of the present specification, the term "interferon" shall refer also to modified interferons and/or recombinantly produced interferons such as peginterferon alfa-2a.

Peginterferon alfa-2a (sold as Pegasys® by Genentech, South San Francisco, USA) is a covalent conjugate of recombinant alfa-2a interferon (having an approximate molecular weight of 20,000 daltons) with a single branched bis-monomethoxy polyethylene glycol (PEG) chain (having an approximate molecular weight of 40,000 daltons). The PEG moiety is linked at a single site to the interferon alfa moiety via a stable amide bond to lysine. Peginterferon alfa-2a has an approximate molecular weight of 60,000 daltons. The advantage of peginterferon alfa-2a over interferons that do not contain the PEG moiety is that peginterferon alfa-2a exhibits a longer half-life, requiring less frequent dosing.

SUMMARY OF THE INVENTION

The present invention relates to a method of treating a patient suffering from a proliferative disorder, comprising administering to the patient: (A) a first component which comprises, as an active agent, Compound I, or a pharmaceutically-acceptable salt thereof; and (B) a second component which comprises, as an active agent, an interferon; the amounts of said active agents being such that the combination thereof is therapeutically-effective in the treatment of said proliferative disorder.

The present invention also relates to a kit comprising: (A) a first component which comprises, as an active agent, Compound I, or a pharmaceutically-acceptable salt thereof; and (B) a second component which comprises, as an active agent, an interferon.

The present invention further relates to a composition comprising: (A) a first component which comprises, as an active agent, Compound I, or a pharmaceutically-acceptable salt thereof; and (B) a second component which comprises, as an active agent, an interferon.

In addition, the present invention relates to the use of Compound I, or a pharmaceutically-acceptable salt thereof, and an interferon for the treatment of a proliferative disorder.

A yet further aspect of the present invention is the use of Compound I, or a pharmaceutically-acceptable salt thereof, and an interferon for the preparation of a medicament for the treatment of a proliferative disorder.

DETAILED DESCRIPTION OF THE INVENTION

Figure 1:
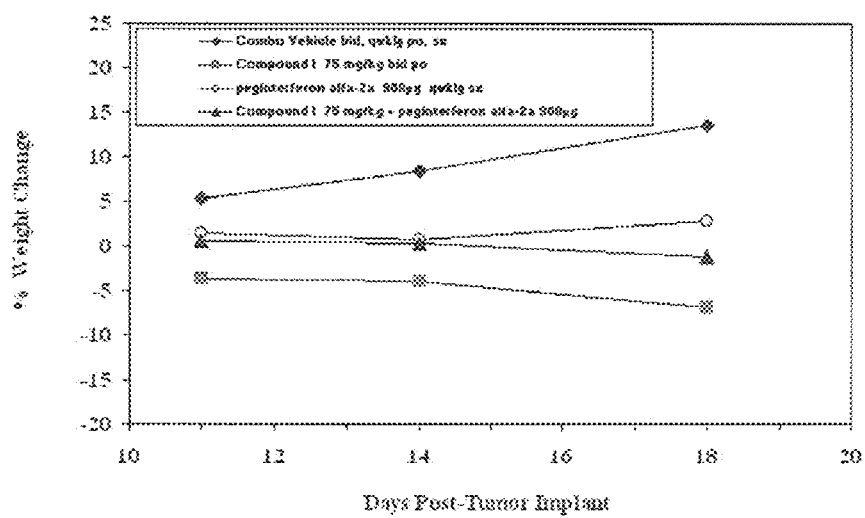
FIG. 1 illustrates the tolerability, as demonstrated by % body weight change, of Compound I 75 mg/kg bid monotherapy, peginterferon alfa-2a 900 µg 1×/wk monotherapy, and Compound I 75 mg/kg bid/peginterferon alfa-2a 900 µg 1×/wk combination therapy.

As stated above, "Compound I" shall herein refer to propane-1-sulfonic acid{3-[5-(4-chloro-phenyl)-1H-pyrrolo[2,3-b]pyridine-3-carbonyl-2,4-difluoro-phenyl]-amide}. This is a compound having the following structure.

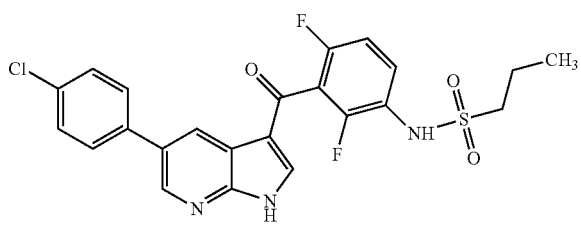 [SMILES: CCCS(=O)(=O)Nc1ccc(F)c(C(=O)c2c[nH]c3ncc(-c4ccc(Cl)cc4)cc23)c1F]

Compound I is a b-Raf kinase inhibitor that specifically targets the V600E mutation of b-Raf.

The "V600E" mutation of b-Raf, as used herein, refers to a mutation in the b-Raf protein wherein the valine residue at residue position 600 of b-Raf is replaced by glutamic acid.

As used herein, the term "pharmaceutically acceptable carrier" indicates that the indicated carrier does not have properties that would cause a reasonably prudent medical practitioner to avoid administration thereof to a patient, taking into consideration the disease or conditions to be treated and the respective route of administration.

As used herein, the term "pharmaceutically acceptable salt" of a compound refers to any conventional salt or base addition salt that retains the biological effectiveness and properties of the compound and which is formed from a suitable non-toxic organic or inorganic acid or organic or inorganic base.

As used herein, the term "therapeutically effective" means an amount of drug, or combination or composition, which is effective for producing a desired therapeutic effect upon administration to a patient, for example, to stem the growth, or result in the shrinkage, of a cancerous tumor or to increase the patient's life span.

The terms "cell proliferative disorder" and "proliferative disorder" refer to disorders that are associated with some degree of abnormal cell proliferation. In one embodiment, the proliferative disorder is cancer.

The terms "cancer" and "cancerous" refer to or describe the physiological condition in mammals that is typically characterized by unregulated cell growth/proliferation. Examples of cancer include, but are not limited to, colorectal cancer, melanoma, and thyroid cancer.

The term "colorectal tumor" or "colorectal cancer" refers to any tumor or cancer of the large bowel, which includes the colon (the large intestine from the cecum to the rectum) and the rectum, including, e.g., adenocarcinomas and less prevalent forms, such as lymphomas and squamous cell carcinomas.

"Inhibiting cell growth or proliferation" means decreasing a cell's growth or proliferation by at least 10%, 20%, 30%, 40%, 50%, 60%, 70%, 80%, 90%, 95%, or 100%, and includes inducing cell death.

The phrase "substantially reduced" or "substantially different," as used herein, refers to a sufficiently high degree of difference between two numeric values (generally one associated with a molecule and the other associated with a reference/comparator molecule) such that one of skill in the art would consider the difference between the two values to be of statistical significance within the context of the biological characteristic measured by said values.

The term "tumor" refers to all neoplastic cell growth and proliferation, whether malignant or benign, and all pre-cancerous and cancerous cells and tissues. The terms "cancer," "cancerous," "cell proliferative disorder," "proliferative disorder," and "tumor" are not mutually exclusive as referred to herein.

"Regression" of a tumor is said to occur following treatment when the volume of said tumor is reduced. If the tumor remains present (tumor volume >0 mm$^3$) but its volume is reduced from what it was at the initiation of treatment, "partial regression" (PR) is said to have occurred. If the tumor is palpably absent following treatment, "complete regression" (CR) is said to have occurred.

The present invention relates to a method of treating a patient suffering from a proliferative disorder, comprising administering to the patient: (A) a first component which comprises, as an active agent, Compound I, or a pharmaceutically-acceptable salt thereof; and (B) a second component which comprises, as an active agent, an interferon; the amount of said active agents being such that the combination thereof is therapeutically-effective in the treatment of said proliferative disorder.

Treatment of a proliferative disorder shall be understood to include maintaining or decreasing tumor size, inducing tumor regression (either partial or complete), inhibiting tumor growth, and/or increasing the life span of a patient suffering from said disorder.

The present invention also relates to a kit or a composition comprising: (A) a first component which comprises, as an active agent, Compound I, or a pharmaceutically-acceptable salt thereof; and (B) a second component which comprises, as an active agent, an interferon. The kit or composition may be used, for example, in the treatment of a proliferative disorder.

In addition, the present invention provides the use of Compound I, or a pharmaceutically-acceptable salt thereof, and an interferon for the treatment of a proliferative disorder.

The invention further provides the use of Compound I, or a pharmaceutically-acceptable salt thereof, and an interferon for the preparation of a medicament for the treatment of a proliferative disorder.

In an embodiment of the present invention, the patient is a human.

In an embodiment of the invention, the proliferative disorder is a solid tumor.

In another embodiment of the invention, the proliferative disorder is a tumor containing the V600E b-Raf mutation.

In a further embodiment of the invention, the tumor is a solid tumor is selected from the group consisting of: colorectal cancer, melanoma, and thyroid cancer and the cancer involves a tumor comprising b-Raf having the V600E mutation.

In yet a further embodiment of the invention, the proliferative disorder is a solid tumor comprising b-Raf having the V600E mutation.

In yet a further embodiment of the invention, the tumor is a solid tumor containing the V600E b-Raf mutation and said tumor is selected from the group consisting of: colorectal cancer, melanoma, and thyroid cancer.

In yet a further embodiment of the invention, the tumor is melanoma.

In yet a further embodiment of the invention, the tumor is melanoma containing the V600E b-Raf mutation.

In yet a further embodiment of the invention, the interferon is selected from the group consisting of: peginterferon alfa-2a, interferon alfa-2a, peginterferon alfa-2b, and interferon alfa-2b.

In yet a further embodiment of the invention, the interferon is peginterferon alfa-2a.

In yet a further embodiment of the invention, the interferon is interferon alfa-2b.

In yet a further embodiment of the invention, the present invention relates to a method of treating a patient suffering from melanoma containing the V600E b-Raf mutation, comprising administering to the patient: (A) a first component which comprises, as an active agent, Compound I, or a pharmaceutically-acceptable salt thereof; and (B) a second component which comprises, as an active agent, peginterferon alfa-2a; the amount of said active agents being such that the combination thereof is therapeutically-effective in the treatment of said melanoma.

The amount of each component administered according to the present method may, but does not have to be therapeutically effective by itself. That is, this invention specifically contemplates combinations wherein the amount of Compound I, or a pharmaceutically-acceptable salt thereof, and/or the amount of interferon, in the combination may be less than the amount that is therapeutically-effective for each active agent when said agent is administered in monotherapy.

Compound I, or a pharmaceutically-acceptable salt thereof, may, for example, be administered orally. Peginterferon alfa-2a may, for example, be administered subcutaneously. The first component and the second component of the present invention are administered in any amount and for any duration that the combined amounts thereof are therapeutically effective in treating a proliferative disorder.

In embodiments of the present invention, Compound I is administered daily at a dosage amount of from about 200 mg/day to about 3000 mg/day, from about 800 mg/day to about 2500 mg/day, from about 1400 mg/day to about 2100 mg/day, about 960 mg/day, about 1440 mg/day, or about 1920 mg/day.

In an embodiment of the present invention, the foregoing amounts of Compound I may be administered as a single dose daily or divided, for example into equal doses (though this is not required), and administered twice daily (bid). For example, Compound I may be administered daily in a dosage amount of from about 100 mg to about 1500 mg bid, from about 400 mg to about 1250 mg bid, from about 700 mg to about 1050 mg bid, about 480 mg bid, about 720 mg bid, or about 960 mg bid.

In an embodiment of the present invention, the administration of Compound I, or a pharmaceutically acceptable salt thereof, occurs until disease progression or unacceptable toxicity.

In an embodiment of the present invention, peginterferon alfa-2a is administered at a dosage of from about 1 μg/week to about 1,000 μg/week, from about 50 μg/week to about 800 μg/week, or from about 90 μg/week to about 630 μg/week. In yet another embodiment, the dosage amount is about 180 μg/week.

In an embodiment of the present invention, the administration of peginterferon alfa-2a occurs until disease relapse, disease progression or unacceptable toxicity. In another embodiment, the peginterferon alfa-2a is administered at the dosage amounts described above for a period of up to 12 months, up to 24 months, up to 36 months, or up to 60 months.

The present invention also provides a method of treating a patient suffering from a proliferative disorder, comprising administering to the patient: (A) a first component which comprises, as an active agent, Compound I in an amount of from about 200 mg/day to about 3000 mg/day, from about 800 mg/day to about 2500 mg/day, from about 1400 mg/day to about 2100 mg/day, about 960 mg/day, about 1440 mg/day, or about 1920 mg/day; and (B) a second component which comprises, as an active agent, peginterferon alfa-2a in an amount of from about 1 μg/week to about 1,000 μg/week, from about 50 μg/week to about 800 μg/week, from about 90 μg/week to about 630 μg/week, or about 180 μg/week. In an embodiment of this invention, the proliferative disorder is a solid tumor, in particular the disorder is selected from the group consisting of: colorectal cancer, melanoma, and thyroid cancer. In another embodiment of this invention, the proliferative disorder involves a tumor comprising b-Raf having the V600E mutation. In a particular embodiment of this invention, the proliferative disorder is melanoma comprising b-Raf having the V600E mutation.

In another aspect of this invention, the components herein described above are administered in conjunction with radiotherapy and/or in conjunction with another active agent.

Compound I exists in its natural state in a crystalline form. However, the amorphous form of the compound has greater solubility in water as compared with the crystalline form and thus has an improved dissolution rate and, therefore, improved bioavailability as compared to the crystalline form. As such, the amorphous form of the compound is preferred. Accordingly, in preferred embodiments of the present invention, Compound I is in substantially amorphous form and, more preferably, in amorphous form. As used herein, the term "substantially amorphous" material embraces material which has no more than about 10% crystallinity; and "amorphous" material embraces material which has no more than about 2% crystallinity.

In an embodiment of the present invention, Compound I is contained in a solid molecular complex formed with hydroxypropyl methyl cellulose acetate succinate (HPMC-AS). As used herein, the term "solid molecular complex" means a composition wherein Compound I is randomly distributed ("molecularly dispersed") within a matrix formed by HPMC-AS. In certain embodiments Compound I is present in the polymer in a final state of subdivision. In certain embodiments, Compound I is molecularly dispersed within the HPMC-AS matrix such that it is immobilized in its amorphous form. By "immobilized", it is meant that the molecules of Compound I interact with molecules of HPMC-AS in such a way that they are held in the aforementioned matrix and prevented from crystal nucleation due to lack of mobility. In some embodiments the polymer may prevent intramolecular hydrogen bonding or weak dispersion forces between two or more molecules of Compound I.

In some embodiments the ratio of the amount by weight of Compound I within the solid molecular complex to the amount by weight of HPMC-AS therein is from about 1:9 to about 5:5. In an embodiment, said ratio is from about 2:8 to about 4:6. In another embodiment, said ratio is about 3:7.

In certain embodiments of the method and kit of the present invention, the first component comprises the aforementioned solid molecular complex of Compound I and HPMC-AS blended with colloidal silicon dioxide. In certain embodiments, the blend is at least 0.5% by weight silicon dioxide. In an embodiment of the present invention, the blend is about 97% complex and about 3% silicon dioxide.

In another embodiment, the first component includes a composition comprising the aforementioned solid molecular complex, either blended or not blended with silicon dioxide as described above, and a pharmaceutically acceptable carrier. In certain embodiments, the aforementioned complex or blend comprising the same is suspended in the carrier. An example of a carrier is hydroxypropylcellulose (HPC). In an embodiment, the vehicle contains about 2% by weight HPC.

Each component may also contain additional agents such as preserving agents, solubilizing agents, stabilizing agents, wetting agents, emulsifying agents, sweetening agents, coloring agents, flavoring agents, salts for varying the osmotic pressure, buffers, coating agents and antioxidants.

In certain embodiments, the first component may comprise a solid molecular complex of Compound I and HPMC-AS blended with colloidal silicon dioxide, hydroxypropylcellulose, Crospovidone (a disintegrating agent), magnesium stearate (a lubricant that may be used in tablet and capsulation operations), and/or croscarmellose sodium (a disintegrating agent).

In an embodiment, the first component is a hard gelatin capsule comprising a solid molecular complex of Compound I and HPMC-AS blended with colloidal silicon dioxide, hydroxypropylcellulose, magnesium stearate, and croscarmellose sodium.

In an embodiment, the first component is a tablet comprising Compound I, or a pharmaceutically acceptable salt thereof. In an embodiment, the tablet comprises a solid molecular complex of Compound I, or a pharmaceutically acceptable salt thereof, and HPMC-AS. The complex may, for example, be blended with colloidal silicon dioxide, hydroxypropylcellulose, magnesium stearate, and croscarmellose sodium. The tablet may, for example, be coated with a film coating. The film coating may, for example, comprise polyvinyl alcohol, titanium dioxide, polyethylene glycol 3350, talc, and iron oxide red.

In certain embodiments, the second component may comprise peginterferon alfa-2a as an injectable solution.

Pegasys® is available as an injectable solution in vials and prefilled syringes. Each 180 μg/1.0 ml vial contains approximately 1.2 ml of solution to deliver 1.0 ml of drug product. Subcutaneous (sc) administration of 1.0 ml delivers 180 μg of drug product (expressed as the amount of interferon alfa-2a), 8.0 mg sodium chloride, 0.05 mg polysorbate 80, 10.0 mg benzyl alcohol, 2.62 mg sodium acetate trihydrate, and 0.0462 mg acetic acid. The solution is colorless to light yellow and the pH is 6.0±0.5. Each 180 μg/0.5 ml prefilled syringe contains 0.6 ml of solution to deliver 0.5 ml of drug product. Subcutaneous (sc) administration of 0.5 ml delivers 180 μg of drug product (expressed as the amount of interferon alfa-2a), 4.0 mg sodium chloride, 0.025 mg polysorbate 80, 5.0 mg benzyl alcohol, 1.3085 mg sodium acetate trihydrate, and 0.0231 mg acetic acid. The solution is colorless to light yellow and the pH is 6.0±0.5.

Applicants have conducted studies using mice containing a human melanoma xenograft.

Applicants found that, while the combination of Compound I at 75 mg/kg bid and peginterferon alfa-2a at 900 μg 1×/wk produced significantly increased life span (ILS) in mice in comparison to what was achieved with 900 μg 1×/wk peginterferon alfa-2a monotherapy, the ILS results were statistically equivalent to what was achieved with Compound I 75 mg/kg bid monotherapy.

In order to unmask the effect of combination therapy, applicants conducted studies in which Compound I was administered at 25 mg/kg bid and peginterferon alfa-2a was administered at 450 μg 1×/wk. In mice, 25 mg/kg bid Compound I achieved 321% increased life span (ILS) and 450 μg 1×/wk peginterferon alfa-2a achieved 114% ILS. By contrast, when a combined therapy of 25 mg/kg bid Compound I and 450 μg 1×/wk peginterferon alfa-2a was administered to mice, 2843% ILS was achieved. As such, ILS achieved by the combination therapy is significantly better than correlative monotherapy results at $p<0.05$.

It is important to note that no increased toxicity was seen in the combination groups and there was no antagonism between the two agents.

These studies indicate that treating patients with a combination of Compound I and peginterferon alfa-2a is superior to treatment with either agent alone, and that combining the two agents allows for reduction in the dose of either agent needed to obtain equivalent or better results.

EXAMPLES

The invention will be more fully understood by reference to the following examples. They should not, however, be construed as limiting the scope of the invention.

Abbreviations used herein are as follows:

| | |
|---|---|
| q.s. | as much as needed |
| x | times |
| po | orally |
| sc | subcutaneously |
| bid | twice daily |
| wk | week |
| BWL | body weight loss |

Example 1

This example describes the formation of a suspension comprising Compound I.

A solid molecular complex comprising Compound I and hydroxypropyl methyl cellulose acetate succinate (HPMC-AS) was first formed.

Compound I and HPMC-AS in a ratio of approximately 3:7, respectively, were dissolved in dimethylacetamide (DMA). The resulting solution was then added with stirring to very cold dilute hydrochloric acid resulting in the co-precipitation of Compound I and HPMC-AS as a solid molecular complex wherein Compound I was present in a nanoparticulate size range. The ratio of DMA to acid was in the range of 1:5 to 1:10.

The co-precipitate was then washed with water to remove DMA, filtered, dried to <2% moisture content and passed through a #30 mesh screen prior to evaluation. The resulting solid molecular complex was 30% by weight Compound I and 70% by weight HPMC.

The complex was then blended with colloidal silicon dioxide (available as Aerosil® 200 from Evonik Industries AG, Essen, Germany) such that, per 100 g of the blend, 97 g was the complex and 3 g was colloidal silicon dioxide.

An aqueous vehicle containing 2% hydroxypropylcellulose (available as Klucel® LF from Aqualon, Wilmington, Del., USA) and 1N HCL at Qs to pH4 for the purpose of pH adjustment was then prepared. 23.2 mL of the vehicle was equilibrated to room temperature and slowly transferred into 773.2 mg of the aforementioned blend. The resulting preparation was then slowly mixed until a homogenous suspension was obtained. The suspension was stored at 2-8° C. and protected from light.

The suspension contained 9.375 mg/mL of Compound I.

Example 2

This example describes an injectable solution of peginterferon alfa-2a.

| Component | Amount |
|---|---|
| Peginterferon alfa-2a | 4.5 mg |
| Benzyl alcohol | 10.0 mg |
| Sodium chloride | 8.00 mg |
| Sodium acetate trihydrate | 2.617 mg |
| Acetic acid, glacial | 0.0462 mg |

-continued

| Component | Amount |
|---|---|
| Polysorbate 80 | 0.05 mg |
| Sodium acetate trihydrate, 10% w/v | q.s. pH 6.0 |
| Acetic acid, 10% w/v | q.s., pH 6.0 |
| Water for injection | q.s. to 1.0 ml |

The solution was stored at 2 to 8° C.

Example 3

Mice were implanted with human LOX-IMVI melanoma cell xenografts. The mice, cell line used, and implantation are described below.

Female athymic Crl:NU-Foxn1nu mice were used for efficacy testing (Charles River, Wilmington, Mass., USA). Mice were 10-12 weeks of age and weighed 23-25 grams. The health of the mice was assessed daily by observation and analysis of blood samples taken from sentinel animals on shared shelf racks. All animals were allowed to acclimate and recover from shipping-related stress for one week. Autoclaved water and irradiated food (5058-ms Pico Lab mouse chow, Purina Mills, Richmond, Ind., USA) were provided ad libitum, and the animals were kept in a 12 hour light and dark cycle. Cages, bedding and water bottles were autoclaved before use and changed weekly. All animal experiments were conducted in accordance with the Guide for the Care and Use of Laboratory Animals, local regulations, and protocols approved by the Roche Animal Care and Use Committee in our AAALAC accredited facility.

LOX-IMVI cells (aka LOX, National Cancer Institute—Bethesda, Md.) were grown in RPMI-1640 medium supplemented with 10% Fetal Bovine Serum (FBS) and 1% of 200 nM L-glutamine, scaled up, harvested, and prepared so that each mouse received $2\times10^6$ cells/0.2 ml calcium and magnesium free phosphate-buffered saline (PBS). Cells were implanted in the subcutaneous right flank of each mouse.

Mice implanted with human xenografts were randomized into eight groups of 10 mice each according to tumor volume so that all groups had similar starting mean tumor volumes. The approximate starting mean tumor volume for this study was 130 $mm^3$.

Example 4

Compound I was formulated as a suspension as described in example 1. Peginterferon alfa-2a was formulated as an injectable solution as described in example 2.

Treatment began on day 5 post-cell implant and ended at day 18 post-cell implant. Four groups of mice developed in example 3 were used. Each group was subjected to a different therapy as follows:
(1) mice receiving Compound I vehicle bid po and peginterferon alfa-2a vehicle 1×/wk sc;
(2) mice receiving Compound I at 75 mg/kg bid bid po;
(3) mice receiving peginterferon alfa-2a at 900 µg 1×/wk sc; and
(4) mice receiving Compound I at 75 mg/kg bid bid po and peginterferon alfa-2a at 900 µg 1×/wk sc.

The Compound I suspension and its corresponding vehicle were dosed using a sterile 1 cc syringe and 18-gauge gavage needle (0.2 ml/animal) twice daily. The peginterferon alfa-2a solution and its corresponding vehicle were dosed using a sterile 1 cc syringe and 26-gauge needle (0.2 ml/animal) once weekly on days 5 and 12 post-cell implant for a total of two injections.

Tumor measurements were taken once or twice per week. All animals were individually followed throughout the experiment.

Weight loss was graphically represented as percent change in mean group body weight, using the formula: $((W-W_0)/W_0)\times100$, where 'W' represents mean body weight of the treated group at a particular day, and '$W_0$' represents mean body weight of the same treated group at initiation of treatment. Maximum weight loss was also represented using the above formula, and indicated the maximum percent body weight loss that was observed at any time during the entire experiment for a particular group.

Efficacy data was graphically represented as the mean tumor volume±standard error of the mean (SEM). In addition, tumor volumes of treated groups were presented as percentages of tumor volumes of the control groups (% T/C), using the formula: $100\times((T-T_0)/(C-C_0))$, where T represented mean tumor volume of a treated group on a specific day during the experiment, $T_0$ represented mean tumor volume of the same treated group on the first day of treatment; C represented mean tumor volume of a control group on the specific day during the experiment, and $C_o$ represented mean tumor volume of the same treated group on the first day of treatment.

Tumor volume (in cubic millimeters) was calculated using the ellipsoid formula: $(D\times(d^2))/2$, where "D" represents the large diameter of the tumor and "d" represents the small diameter.

Also, tumor regression and/or percent change in tumor volume was calculated using the formula: $((T-T_0)/T_0)\times100$, where 'T' represents mean tumor volume of the treated group at a particular day, and '$T_0$' represents mean tumor volume of the same treated group at initiation of treatment.

Statistical analysis was determined by the rank sum test and One Way Anova and a post-hoc Bonferroni t-test (SigmaStat, version 2.0, Jandel Scientific, San Francisco, Calif., USA). Differences between groups were considered to be significant when the probability value (p) was ≤0.05.

For survival assessment, the percent of increased life space (ILS) was calculated as: 100×[(median survival day of treated group−median survival day of control group)/median survival day of control group]. Median survival was determined utilizing Kaplan Meier survival analysis. Survival in treated groups was statistically compared with the vehicle group and survival comparisons were done between groups using the log-rank test (Graph Pad Prism, La Jolla, Calif., USA). Differences between groups were considered significant when the probability value (p) was ≤0.05.

Toxicity

No signs of toxicity were noted in any dose group in any of the studies described as assessed by measuring changes in body weight and gross observation of individual animals. These results are depicted in Table 1 and FIG. 1.

TABLE 1

| Group | Frequency | Route | % Change in Body Weight at end of Study Day 18 | Max % Weight Loss | Max % Weight Gain | # animals ≥ 20% BWL | Mortality |
| --- | --- | --- | --- | --- | --- | --- | --- |
| Combo Vehicle | bid, 1x/wk | po, sc | 13.5 | 5.3 | 13.5 | 0 | 0 |
| Compound I 75 mg/kg | bid | po | −7.0 | −7.0 | −3.6 | 0 | 0 |
| Peginterferon alfa-2a 900 µg | 1x/wk | sc | 2.7 | 0.7 | 2.7 | 0 | 0 |
| Compound I 75 mg/kg + Peginterferon alfa-2a 900 µg | bid, 1x/wk | po, sc | −1.1 | −1.1 | 0.5 | 0 | 0 |

Tumor Growth Inhibition (TGI)

Figure 2:
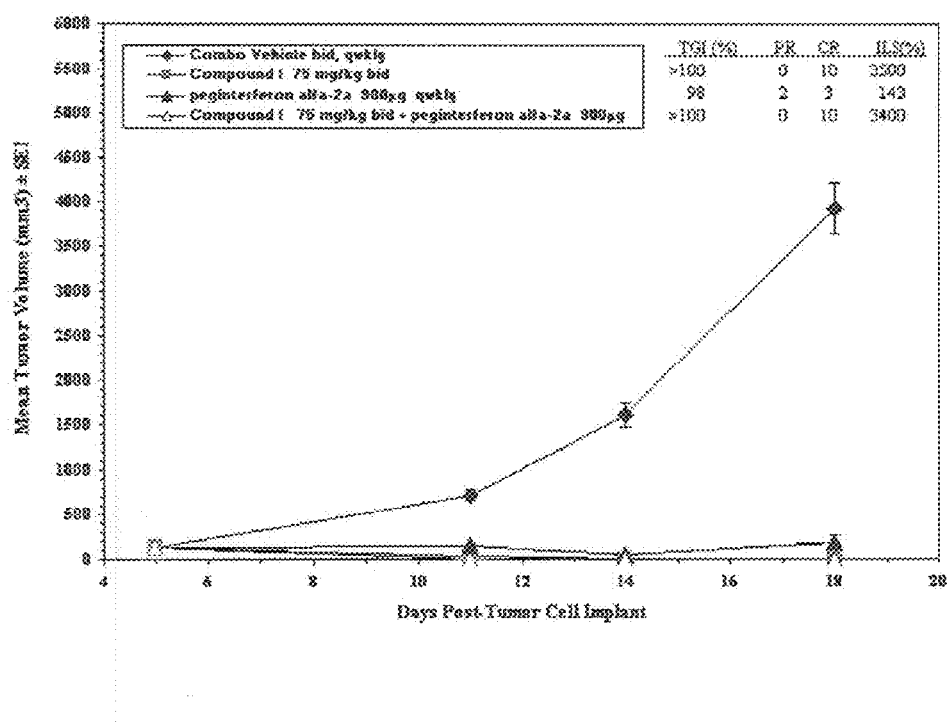
FIG. 2 illustrates the antitumor activity, as demonstrated by tumor volume, of Compound I 75 mg/kg bid monotherapy, peginterferon alfa-2a 900 µg 1×/wk monotherapy, and Compound I 75 mg/kg bid/peginterferon alfa-2a 900 µg 1×/wk combination therapy.

The group receiving Compound I monotherapy at 75 mg/kg bid exhibited greater than 100% TGI with 10 out of 10 complete regressions (CRs). The group receiving peginterferon alfa-2a monotherapy at 900 µg 1x/wk exhibited 98% TGI, 2 partial regressions (PRs) and 3 CRs out of 10. The group receiving combination therapy of Compound I at 75 mg/kg bid and peginterferon alfa-2a at 900 µg 1x/wk exhibited greater than 100% TGI with 10 out of 10 CRs. See Tables 2 and 3 and FIG. 2.

Assessment of Survival

Figure 3:
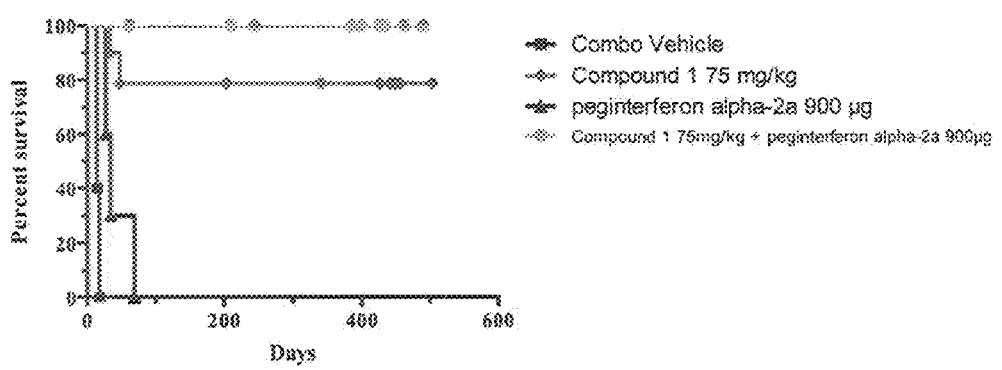
FIG. 3 illustrates the effect on survival, as demonstrated by percentage of surviving mice over time, of Compound I 75 mg/kg bid monotherapy, peginterferon alfa-2a 900 µg 1×/wk monotherapy, and Compound I 75 mg/kg bid/peginterferon alfa-2a 900 µg 1×/wk combination therapy.

The group receiving Compound I monotherapy at 75 mg/kg bid exhibited 3500% increased life span (ILS). The group receiving peginterferon alfa-2a monotherapy at 900 µg 1x/wk exhibited 143% ILS. The group receiving combination therapy of Compound I at 75 mg/kg bid and peginterferon alfa-2a at 900 µg 1x/wk exhibited 3400% ILS. See Table 4 and FIG. 3.

TABLE 2

| Group | Frequency | Route | Mean Tumor Volume (mm$^3$) Start Study DAY: 5 | SEM | SD | Mean Tumor Volume (mm$^3$) End Study DAY: 18 | SD | SEM |
| --- | --- | --- | --- | --- | --- | --- | --- | --- |
| Combo Vehicle | bid, 1x/wk | po, sc | 132.83 | ±2.65 | ±8.38 | 3918.69 | ±914.15 | ±289.08 |
| Compound I 75 mg/kg | bid | po | 134.36 | ±2.52 | ±7.98 | 0.00 | ±0.00 | ±0.00 |
| Peginterferon alfa-2a 900 µg | 1x/wk | sc | 131.77 | ±2.84 | ±8.98 | 193.98 | ±220.41 | ±69.70 |
| Compound I 75 mg/kg + Peginterferon alfa-2a 900 µg | bid, 1x/wk | po, sc | 131.79 | ±1.68 | ±5.32 | 0.00 | ±0.00 | ±0.00 |

TABLE 3

| Group | % T/C end of study Day: 18 | % Inhibition end of study Day: 18 | P value End of study Day: 18 | Average % Regression per Group | Partial Regression | Complete Regression | Animal per Group | % Tumor Growth Inhibition |
| --- | --- | --- | --- | --- | --- | --- | --- | --- |
| Combo Vehicle | — | — | — | — | 0 | 0 | 10 | — |
| Compound I 75 mg/kg bid | −4 | regression | <0.001 | 100 | 0 | 10 | 10 | >100 |
| Peginterferon alfa-2a 900 µg 1x/wk | 2 | 98 | <0.001 | — | 2 | 3 | 10 | 98 |
| Compound I 75 mg/kg bid + Peginterferon alfa-2a 900 µg 1x/wk | −3 | regression | <0.001 | 100 | 0 | 10 | 10 | >100 |

TABLE 4

ILS Calculations

| Group | 50% Treatment Days | 50% Vehicle Days | % ILS | P value |
|---|---|---|---|---|
| Combo Vehicle | — | — | — | — |
| Compound I 75 mg/kg bid | 504 | 14 | 3500 | <0.0001 |
| Peginterferon alfa-2a 900 µg 1x/wk | 34 | 14 | 143 | <0.0001 |
| Compound I 75 mg/kg bid + Peginterferon alfa-2a 900 µg 1x/wk | 490 | 14 | 3400 | <0.0001 |

Statistical Analysis

The % TGI in the Compound I 75 mg/kg bid/peginterferon alfa-2a 900 µg 1x/wk combination therapy group was statistically superior to that of the peginterferon alfa-2a 900 µg 1x/wk monotherapy group but equivalent to that of the Compound I 75 mg/kg bid monotherapy group. The % ILS in the Compound I 75 mg/kg bid/peginterferon alfa-2a 900 µg 1x/wk combination therapy group was statistically superior to that of the peginterferon alfa-2a 900 µg 1x/wk monotherapy group but equivalent to that of the Compound I 75 mg/kg bid monotherapy group. See Table 5.

TABLE 5

| Treatment versus Treatment | | TGI p value* | ILS p value** |
|---|---|---|---|
| Compound I 75 mg/kg bid | Peginterferon alfa-2a 900 µg 1x/wk | <0.05 | <0.0001 |
| Compound I 5 mg/kg bid | Compound I 75 mg/kg bid + Peginterferon alfa-2a 900 µg 1x/wk | >0.05 | 0.1343 |
| Peginterferon alfa-2a 900 µg 1x/wk | Compound I 75 mg/kg bid + Peginterferon alfa-2a 900 µg 1x/wk | <0.05 | <0.0001 |

*One-Way ANOVA, post-hoc Bonferroni
**Breslow-Gehan-Wilcoxon

Example 5

Compound I was formulated as a suspension as described in example 1. The Compound I vehicle was 2.0 grams of Klucel LF in Peginterferon alfa-2a was formulated as an injectable solution as described in example 2.

Treatment began on day 6 post-cell implant and ended at day 19 post-cell implant. Four groups of mice developed in example 3 were used. The treatment groups were as follows:
(1) mice receiving Compound I vehicle bid po and peginterferon alfa-2a vehicle 1x/wk sc;
(2) mice receiving Compound I at 25 mg/kg bid po;
(3) mice receiving peginterferon alfa-2a at 450 µg 1x/wk sc; and
(4) mice receiving Compound I at 25 mg/kg bid and peginterferon alfa-2a at 450 µg 1x/wk.

The Compound I suspension and its corresponding vehicle were dosed using a sterile 1 cc syringe and 18-gauge gavage needle (0.2 ml/animal) twice daily. The peginterferon alfa-2a solution and its corresponding vehicle were dosed using a sterile 1 cc syringe and 26-gauge needle (0.2 ml/animal) once weekly on days 6 and 13 post-cell implant for a total of two injections.

Tumor measurements were taken once or twice per week. All animals were individually followed throughout the experiment.

Weight loss was graphically represented as percent change in mean group body weight, using the formula: $((W-W_0)/W_0) \times 100$, where 'W' represents mean body weight of the treated group at a particular day, and '$W_0$' represents mean body weight of the same treated group at initiation of treatment. Maximum weight loss was also represented using the above formula, and indicated the maximum percent body weight loss that was observed at any time during the entire experiment for a particular group.

Efficacy data was graphically represented as the mean tumor volume±standard error of the mean (SEM). In addition, tumor volumes of treated groups were presented as percentages of tumor volumes of the control groups (% T/C), using the formula: $100 \times ((T-T_0)/(C-C_0))$, where T represented mean tumor volume of a treated group on a specific day during the experiment, $T_0$ represented mean tumor volume of the same treated group on the first day of treatment; C represented mean tumor volume of a control group on the specific day during the experiment, and $C_0$ represented mean tumor volume of the same treated group on the first day of treatment.

Tumor volume (in cubic millimeters) was calculated using the ellipsoid formula: $(D \times (d2))/2$, where "D" represents the large diameter of the tumor and "d" represents the small diameter.

Also, tumor regression and/or percent change in tumor volume was calculated using the formula: $((T-T_0)/T_0) \times 100$, where 'T' represents mean tumor volume of the treated group at a particular day, and '$T_0$' represents mean tumor volume of the same treated group at initiation of treatment.

Statistical analysis was determined by the rank sum test and One Way Anova and a post-hoc Bonferroni t-test (SigmaStat, version 2.0, Jandel Scientific, San Francisco, Calif., USA). Differences between groups were considered to be significant when the probability value (p) was <0.05.

For survival assessment, the percent of increased life space (ILS) was calculated as: $100 \times [$(median survival day of treated group−median survival day of control group)/median survival day of control group]. Median survival was determined utilizing Kaplan Meier survival analysis. Survival in treated groups was statistically compared with the vehicle group and survival comparisons were done between groups using the log-rank test (Graph Pad Prism, La Jolla, Calif., USA). Differences between groups were considered significant when the probability value (p) was ≤0.05.

Toxicity

Figure 4:
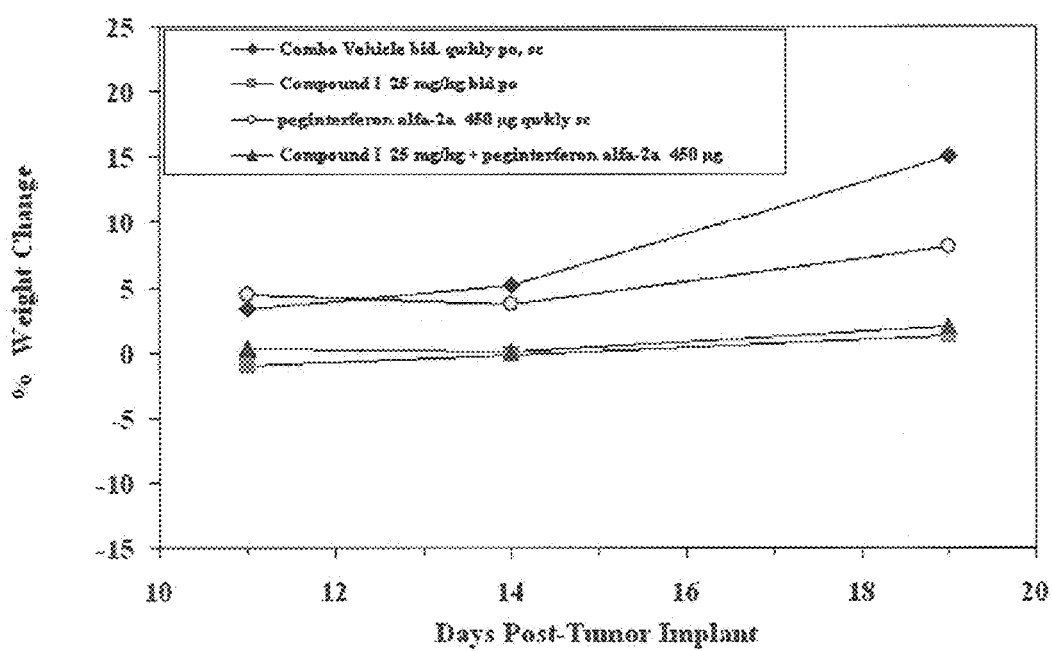
FIG. 4 illustrates the tolerability, as demonstrated by % body weight change, of Compound I 25 mg/kg bid monotherapy, peginterferon alfa-2a 450 µg 1×/wk monotherapy, and Compound I 25 mg/kg bid/peginterferon alfa-2a 450 µg 1×/wk combination therapy.

No signs of toxicity were noted in any dose group in any of the studies described as assessed by measuring changes in body weight and gross observation of individual animals. These results are depicted in Table 6 and FIG. 4.

TABLE 6

| Group | Frequency | Route | % Change in Body Weight at end of Study Day 19 | Max % Weight Loss | Max % Weight Gain | # animals ≥ 20% BWL | Mortality |
|---|---|---|---|---|---|---|---|
| Combo Vehicle | bid, 1x/wk | po, sc | 15.1 | 3.3 | 15.1 | 0 | 0 |
| Compound I 25 mg/kg | bid | po | 1.3 | −1.0 | 1.3 | 0 | 0 |
| Peginterferon alfa-2a 450 µg | 1x/wk | sc | 8.1 | 3.7 | 8.1 | 0 | 0 |
| Compound I 25 mg/kg + Peginterferon alfa-2a 450 µg | bid, 1x/wk | po, sc | 2.1 | 0.1 | 2.1 | 0 | 0 |

Tumor Growth Inhibition (TGI)

Figure 5:
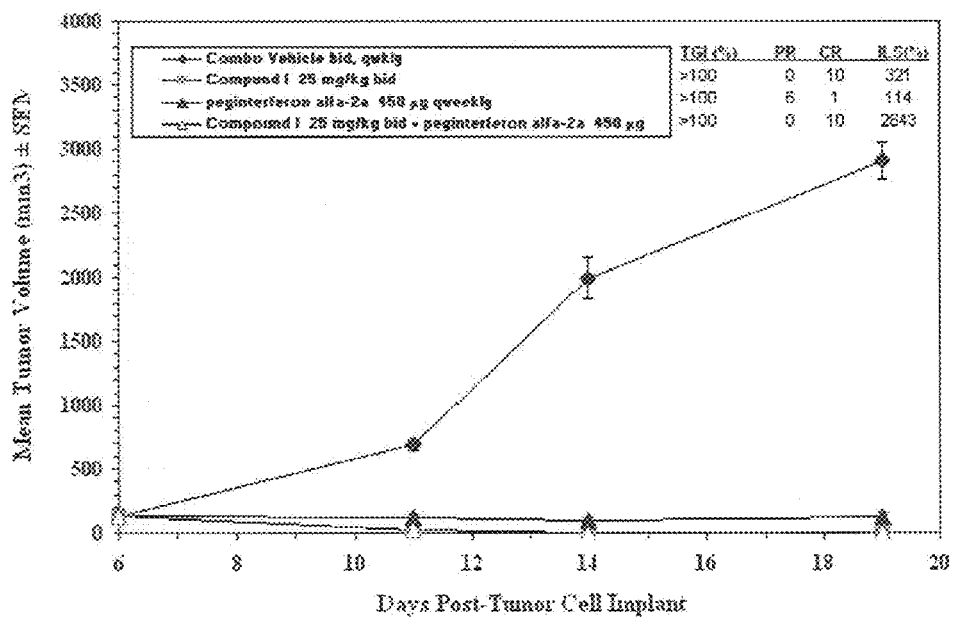
FIG. 5 illustrates the antitumor activity, as demonstrated by tumor volume, of Compound I 25 mg/kg bid monotherapy, peginterferon alfa-2a 450 µg 1×/wk monotherapy, and Compound I 25 mg/kg bid/peginterferon alfa-2a 450 µg 1×/wk combination therapy.

The group receiving Compound I monotherapy at 25 mg/kg bid exhibited greater than 100% TGI with 10 out of 10 CRs. The group receiving peginterferon alfa-2a monotherapy at 450 µg 1x/wk exhibited greater than 100% TGI, 6 PRs and 1 CR out of 10. The group receiving combination therapy of Compound I at 25 mg/kg bid and peginterferon alfa-2a at 450 µg 1x/wk exhibited greater than 100% TGI with 10 out of 10 complete regressions (CRs). See Tables 7 and 8 and FIG. 5.

Assessment of Survival

Figure 6:
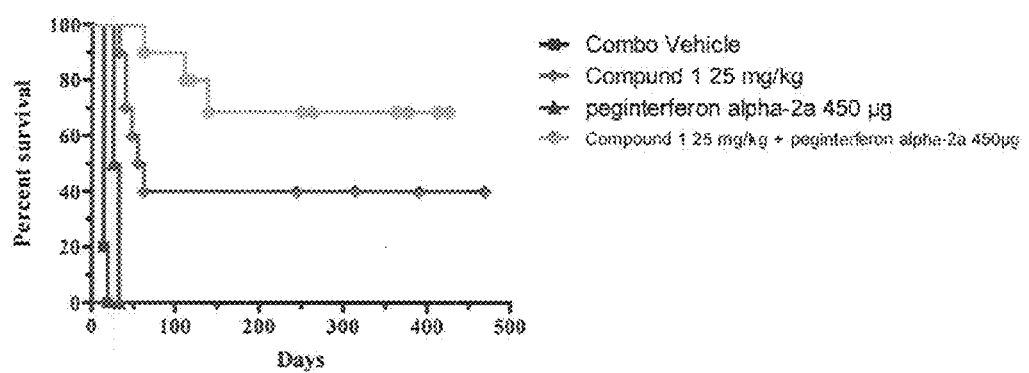
FIG. 6 illustrates the effect on survival, as demonstrated by percentage of surviving mice over time, of Compound I 25 mg/kg bid monotherapy, peginterferon alfa-2a 450 µg 1×/wk monotherapy, and Compound I 25 mg/kg bid/peginterferon alfa-2a 450 µg 1×/wk combination therapy.

The group receiving Compound I monotherapy at 25 mg/kg bid exhibited 321% increased life span (ILS). The group receiving peginterferon alfa-2a monotherapy at 450 µg 1x/wk exhibited 114% ILS. The group receiving combination therapy of Compound I at 25 mg/kg bid and peginterferon alfa-2a at 450 µg 1x/wk exhibited 2843% ILS. See Table 9 and FIG. 6.

TABLE 7

| Group | Frequency | Route | Mean Tumor Volume (mm$^3$) Start Study DAY: 6 | SEM | SD | Mean Tumor Volume (mm$^3$) End Study DAY: 19 | SD | SEM |
|---|---|---|---|---|---|---|---|---|
| Combo Vehicle | bid, 1x/wk | po, sc | 130.71 | ±1.46 | ±4.63 | 2906.48 | ±463.14 | ±146.46 |
| Compound I 25 mg/kg | bid | po | 131.02 | ±2.06 | ±6.52 | 0.00 | ±0.00 | ±0.00 |
| Peginterferon alfa-2a 450 µg | 1x/wk | sc | 131.12 | ±1.19 | ±3.77 | 122.93 | ±117.57 | ±37.18 |
| Compound I 25 mg/kg + Peginterferon alfa-2a 450 µg | bid, 1x/wk | po, sc | 132.29 | ±1.53 | ±4.84 | 0.00 | ±0.00 | ±0.00 |

TABLE 8

| Group | % T/C end of study Day: 19 | % Inhibition end of study Day: 19 | P value End of study Day: 19 | Average % Regression per Group | Partial Regression | Complete Regression | Animals per Group | % Tumor Growth Inhibition |
|---|---|---|---|---|---|---|---|---|
| Combo Vehicle | — | — | — | — | 0 | 0 | 10 | — |
| Compound I 25 mg/kg bid | −5 | regression | <0.001 | 100 | 0 | 10 | 10 | >100 |
| Peginterferon alfa-2a 450 µg 1x/wk | 0 | regression | <0.001 | 6 | 6 | 1 | 10 | >100 |
| Compound I 25 mg/kg bid + Peginterferon alfa-2a 450 µg 1x/wk | −5 | regression | <0.001 | 100 | 0 | 10 | 10 | >100 |

TABLE 9

| | ILS Calculations | | | |
|---|---|---|---|---|
| Group | 50% Treatment Days | 50% Vehicle Days | % ILS | P value |
| Combo Vehicle | — | — | — | — |
| Compound I 25 mg/kg bid | 59 | 14 | 321 | <0.0001 |
| Peginterferon alfa-2a 450 µg 1x/wk | 30 | 14 | 114 | <0.0001 |
| Compound I 25 mg/kg bid + Peginterferon alfa-2a 450 µg 1x/wk | 412 | 14 | 2843 | <0.0001 |

The % TGI in the Compound I 25 mg/kg bid/peginterferon alfa-2a 450 µg 1x/wk combination therapy group was statistically superior to that of the peginterferon alfa-2a 450 µg 1x/wk monotherapy group but equivalent to that of the Compound I 25 mg/kg bid monotherapy group. The % ILS in the Compound I 25 mg/kg bid/peginterferon alfa-2a 450 µg 1x/wk combination therapy group was statistically superior to that each monotherapy group. See Table 10.

TABLE 10

| Treatment versus Treatment | | TGI p value* | ILS p value** |
|---|---|---|---|
| Compound I 25 mg/kg bid | Peginterferon alfa-2a 450 µg 1x/wk | <0.05 | <0.0001 |
| Compound I 25 mg/kg bid | Compound I 25 mg/kg bid + Peginterferon alfa-2a 450 µg 1x/wk | >0.05 | 0.0464 |
| Peginterferon alfa-2a 450 µg 1x/wk | Compound I 25 mg/kg bid + Peginterferon alfa-2a 450 µg 1x/wk | <0.05 | <0.0001 |

*One-Way ANOVA, post-hoc Bonferroni
**Breslow-Gehan-Wilcoxon

The invention claimed is:

1. A method of treating a patient suffering from a proliferative disorder, comprising administering to the patient: (A) a first component which comprises, as an active agent, propane-1-sulfonic acid{3-[5-(4-chloro-phenyl)-1H-pyrrolo[2,3-b]pyridine-3-carbonyl-2,4-difluoro-phenyl]amide}, or a pharmaceutically acceptable salt thereof; and (B) a second component which comprises, as an active agent, peginterferon alfa-2a;
wherein said propane-1-sulfonic acid{3-[5-(4-chloro-phenyl)-1H-pyrrolo[2,3-b]pyridine-3-carbonyl-2,4-difluoro-phenyl]amide} is administered in an amount of from about 1700 mg/day to about 2100 mg/day, wherein said amount is about 25 mg/kg, and
said peginterferon alfa-2a is administered in an amount of from about 180 µg/week to about 630 µg/week, and
wherein said proliferative disorder is selected from the group consisting of: colorectal cancer, melanoma, and thyroid cancer, wherein said cancer involves a tumor comprising b-Raf having the V600E mutation.

2. A method according to claim 1 wherein said patient is a human.

3. A method according to claim 1 wherein said proliferative disorder is melanoma containing the V600E b-Raf mutation.

4. A method according to claim 1 wherein propane-1-sulfonic acid{3-[5-(4-chloro-phenyl)-1H-pyrrolo[2,3-b]pyridine-3-carbonyl-2,4-difluoro-phenyl]amide}, or a pharmaceutically acceptable salt thereof, is substantially in amorphous form.

5. A method according to claim 1 wherein propane-1-sulfonic acid{3-[5-(4-chloro-phenyl)-1H-pyrrolo[2,3-b]pyridine-3-carbonyl-2,4-difluoro-phenyl]amide}, or a pharmaceutically acceptable salt thereof, is in amorphous form.

6. A method according to claim 1 wherein propane-1-sulfonic acid{3-[5-(4-chloro-phenyl)-1H-pyrrolo[2,3-b]pyridine-3-carbonyl-2,4-difluoro-phenyl]amide}, or a pharmaceutically acceptable salt thereof, is contained in a solid molecular complex formed with hydroxypropyl methyl cellulose acetate succinate such that it is immobilized in its amorphous form.

7. A method according to claim 6 wherein the amounts of propane-1-sulfonic acid{3-[5-(4-chloro-phenyl)-1H-pyrrolo[2,3-b]pyridine-3-carbonyl-2,4-difluoro-phenyl]amide}, or a pharmaceutically acceptable salt thereof, are hydroxypropyl methyl cellulose acetate succinate in said complex are in a ratio of from about 1:9 to about 5:5, respectively.

8. A method according to claim 6 wherein the amounts of propane-1-sulfonic acid{3-[5-(4-chloro-phenyl)-1H-pyrrolo[2,3-b]pyridine-3-carbonyl-2,4-difluoro-phenyl]amide}, or a pharmaceutically acceptable salt thereof, and hydroxypropyl methyl cellulose acetate succinate in said complex are in a ratio of about 3:7, respectively.

9. A method according to claim 6 wherein said first component comprises a blend wherein about 97% by weight of the blend is said complex and about 3% by weight of the blend is silicon dioxide.

10. A method according to claim 6 wherein said first component comprises a suspension of said complex in a pharmaceutically acceptable carrier.

11. A method according to claim 1 wherein said first component comprises a tablet comprising a solid molecular complex of propane-1-sulfonic acid{3-[5-(4-chloro-phenyl)-1H-pyrrolo[2,3-b]pyridine-3-carbonyl-2,4-difluoro-phenyl]amide}, or a pharmaceutically acceptable salt thereof, and hydroxypropyl methyl cellulose acetate succinate.

* * * * *